United States Patent
Granger et al.

(10) Patent No.: US 8,685,239 B2
(45) Date of Patent: Apr. 1, 2014

(54) SEPARATION DEVICE WITH INTEGRAL GUARD COLUMN

(75) Inventors: Jennifer Harnisch Granger, Northborough, MA (US); Robert Plumb, Milford, MA (US)

(73) Assignee: Waters Technologies Corporation, Milford, MA (US)

( * ) Notice: Subject to any disclaimer, the term of this patent is extended or adjusted under 35 U.S.C. 154(b) by 2203 days.

(21) Appl. No.: 11/329,759

(22) Filed: Jan. 11, 2006

(65) Prior Publication Data

US 2006/0186029 A1    Aug. 24, 2006

Related U.S. Application Data

(63) Continuation of application No. PCT/US2004/022374, filed on Jul. 12, 2004.

(60) Provisional application No. 60/487,123, filed on Jul. 14, 2003.

(51) Int. Cl.
*B01D 15/22* (2006.01)
*G01N 30/60* (2006.01)

(52) U.S. Cl.
CPC ............. *B01D 15/22* (2013.01); *G01N 30/60* (2013.01); *G01N 30/6065* (2013.01)
USPC ....................................... 210/198.2; 210/656

(58) Field of Classification Search
CPC ..... B01D 15/22; G01N 30/60; G01N 30/6065
USPC ............................ 210/198.2, 635, 656, 502.1
See application file for complete search history.

(56) References Cited

U.S. PATENT DOCUMENTS 2,723,756 A * 11/1955 Miller et al. ................. 210/656
4,250,035 A *  2/1981 McDonald et al. ........ 210/198.2

(Continued)

FOREIGN PATENT DOCUMENTS

JP    63-179250 A    7/1988
JP    63-179250 A    7/1988

(Continued)

OTHER PUBLICATIONS

Tang (Journal of Chromatography A, 887 (2000) 265-275).*

(Continued)

*Primary Examiner* — Ernest G Therkorn
(74) *Attorney, Agent, or Firm* — Schmeiser, Olsen & Watts LLP (57) ABSTRACT

A separation device is formed of a first tube with a cylindrical wall enclosing a chamber having a first diameter, where the device has a first end for discharging a fluid and a second end for receiving a fluid. At least two stationary phase medias are packed into the chamber with separating frits between the medias. At least one end frit element, secured to an inner surface of the first tube contains the media in its section of the chamber and allows the beds formed of the media to be formed and packed. When the separation device so constructed forms a nanocolumn with a guard bed, the guard bed may be cleaved from the separation device extending the useful life of the nanocolumn. When the separation device so constructed comprises two analytical sections, and a plurality of guard beds, complex analysis may be performed on a column having an extended useful life.

19 Claims, 10 Drawing Sheets

(56) References Cited

U.S. PATENT DOCUMENTS

| | | | |
|---|---|---|---|
| 4,280,905 A * | 7/1981 | Gunkel et al. | 210/198.2 |
| 4,301,139 A * | 11/1981 | Feingers et al. | 436/500 |
| 4,476,017 A * | 10/1984 | Scharff et al. | 210/94 |
| 4,636,316 A | 1/1987 | Harris et al. | |
| 4,719,011 A * | 1/1988 | Shalon et al. | 210/198.2 |
| 4,737,465 A * | 4/1988 | Bond et al. | 436/73 |
| 5,071,769 A | 12/1991 | Kundu et al. | |
| 5,667,676 A * | 9/1997 | Alaska | 210/198.2 |
| 5,772,889 A * | 6/1998 | Gjerde et al. | 210/635 |
| 5,908,552 A * | 6/1999 | Dittmann et al. | 210/198.2 |
| 6,139,733 A | 10/2000 | Hargro et al. | |
| 6,162,362 A | 12/2000 | Ma et al. | |
| 6,436,284 B1 * | 8/2002 | Leavesley et al. | 210/198.2 |
| 6,562,744 B1 * | 5/2003 | Nakanishi et al. | 501/39 |
| 6,585,939 B1 * | 7/2003 | Dapprich | 422/99 |
| 6,632,655 B1 * | 10/2003 | Mehta et al. | 506/14 |
| 6,649,051 B1 * | 11/2003 | Jamalabadi et al. | 210/198.2 |
| 6,783,680 B2 * | 8/2004 | Malik | 210/635 |
| 6,875,348 B2 * | 4/2005 | Zare et al. | 210/198.2 |
| 7,192,629 B2 * | 3/2007 | Lammertink et al. | 428/36.9 |
| 2002/0125193 A1 * | 9/2002 | Tang et al. | 210/656 |
| 2002/0158022 A1 * | 10/2002 | Huang et al. | 210/656 |
| 2002/0179513 A1 * | 12/2002 | Willis et al. | 210/198.2 |
| 2003/0150811 A1 * | 8/2003 | Walter et al. | 210/656 |

FOREIGN PATENT DOCUMENTS

| | | |
|---|---|---|
| JP | 2001-24920 A | 9/2001 |
| JP | 2001-24920 A | 9/2001 |
| JP | 2001-330598 | 11/2001 |
| WO | 99/29388 | 6/1999 |
| WO | 00/10675 | 3/2000 |
| WO | 00/10675 A1 | 3/2000 |
| WO | 01/57516 | 8/2001 |

OTHER PUBLICATIONS

Tang (J. High Resol. Chromatogr. 2000, 23 (1) 73-80).*
Tang (Journal of Chromatography A, 837 (1999) 35-50).*
Japanese Office Action, dated Jun. 15, 2010, for counterpart JP patent application No. 2006-520259 (10 pages).

* cited by examiner

SEPARATION DEVICE WITH INTEGRAL GUARD COLUMN

CROSS REFERENCE TO RELATED APPLICATIONS

This application is a continuation of PCT/US04/22374, filed Jul. 12, 2004, which, in turn, claims the benefit of U.S. Patent Application No. 60/487,123 filed Jul. 14, 2003. The contents of the aforementioned application are hereby expressly incorporated herein by reference in its entirety.

STATEMENT ON FEDERALLY SPONSORED RESEARCH

N/A

FIELD OF THE INVENTION

The present invention relates to columns used for high-pressure liquid chromatography (HPLC). The invention has particular advantages in extending the useful life of capillary-sized HPLC columns.

BACKGROUND OF THE INVENTION

High-pressure liquid chromatography (HPLC) is a process used for separating one or more compounds from a chemical mixture. The HPLC process consists of passing the mixture through a stationary packing material, under the influence of a high-pressure transport liquid, and separating the compounds by selective affinity, sieving, adsorption or partitioning. The packing is typically housed within a chamber formed in a cylindrical column and is typically held in place by frits at either end of the chamber. A guard column, either as a distinct mechanism or as a column butted against the HPLC column, can be used to protect the HPLC column from physical or chemical contamination.

The guard column traps impurities or particulates in the sample mixture or in the transport fluid before the impurities or particulates can reach the HPLC column and thereby extends the operable life of the HPLC column. It is desirable to be able to remove a guard column. The advantage of the replaceable guard column is that the HPLC column, which is substantially more expensive than the guard column, does not have to be replaced as often. One concern with guard columns in HPLC equipment is assuring that the connection between the guard column and the HPLC column is sealable and removable. At the high pressures used, simple connection and sealing mechanisms have not sufficed. Therefore, the attachment mechanism increases the overall cost of the column.

As HPLC is performed on more minute quantities of samples, the size of the columns is reduced. Nanocolumns of 75 µm ID are commonly used for small samples. The use of 75 µm ID nanocolumns is often a challenge to the user who needs to analyze complex or "dirty" samples. The nanocolumns loaded with such samples frequently block after one or two injections and are rendered useless for further analysis. Due to the small scale of the nanocolumns, any guard column used with the nanocolumns would have to be installed with virtually no dead space in order to avoid bandspreading. Such guard columns have not been available. In addition, any joining mechanism for attaching a guard column to a nanocolumn must withstand high pressures even though the joining mechanism needs to be very small.

In another aspect of HPLC, there are occasions when it is advantageous to create a column having two distinct analytical regions. These regions must be precisely formed as to composition and length and separated by a neutral material, typically a frit, in order to accomplish a specific separation. As the inside diameter of the cylinder forming the column is reduced, the ability to form separate analytical regions becomes compromised. In nanocolumns, it has not been possible to separate the regions. Consequently, such multi-use nanocolumns are not commercially available. In a research setting, the only multi-use columns that have been fabricated do not have a definite demarcation between the analytical regions. There is an area that is a mixture of the two media at the junction that renders these multi-use columns irreproducible.

There is currently a need to extend the life of nanocolumns even when they are used to analyze complex samples.

SUMMARY OF THE INVENTION

The present invention is directed to a separation device comprising a first tube having a cylindrical wall with an inner surface defining a chamber with a first diameter, and an exterior surface defining a second diameter. One end of the tube receives a fluid and the other end discharges the fluid. The chamber has a first section and at least one second section, with the first section adapted for containing a first media and the second section(s) adapted for containing a second media. When a first and second media are contained within the respective sections, a separating frit element is disposed within the first tube between the sections to separate the medias. At least one end frit element is secured to the inner surface of the first tube to contain one of the medias in the first tube.

In one embodiment, the at least one frit element is a second tube having a second cylindrical wall with a second inner surface defining a cavity with a third diameter, a second exterior surface defining a fourth diameter, a third end and a fourth end. The fourth diameter is slightly smaller than the first diameter so the second tube can be inserted in the first tube. When the second tube is installed in the first tube, the second tube exterior surface cooperates with the inner surface to prevent the media from passing between the surfaces. In one instance, the difference between the fourth diameter and the first diameter is approximately 10 µm. In one instance, the second tube used as a separating frit has a length of approximately 1 cm. In one instance, the third diameter is approximately 20% of the first diameter preventing the media form passing through the cavity because of the keystone effect. In one embodiment, the ends of the second tube are oriented perpendicular to a length of the second tube allowing the end frit elements to be aligned with the ends of the first tube so no dead space is formed thereby limiting bandspreading.

In one embodiment, the end frit element disposed in the end for discharging fluid is formed as a transfer tube for transporting the fluid from the separating device. In one embodiment, the separation device is made with the first tube as a capillary, typically formed of fused silica. The internal diameter of the separation device is between 25 µm and 180 µm, with a preferred range of between 70 µm and 110 µm.

In an alternate embodiment an end frit element is formed as an immobilized stationary phase, where the stationary phase material is suspended in a polymeric network. When the polymeric network is a cross-linked poly(diorganosiloxane) (PDMS) the PDMS frit is formed in situ. In one embodiment, the at least one separating frit is composed of a layer of glass microspheres.

In one embodiment, the separating device is formed with the first section formed as a first analytical bed and a second section formed as a guard bed. In another embodiment, the separating device is formed with the first section formed as a first analytical bed and a second section formed as a second analytical bed. This embodiment, in some instances, further comprises at least an additional section in the chamber, with the additional section adapted for containing a third media. The embodiment uses at least a second separating frit element, the additional separating frit element disposed between the medias in the second sections. The additional second section allows for various configurations of the separating device with the first media formed as a first analytical bed, the second media formed as a second analytical bed or as a guard bed and the third media formed as a guard bed. Up to two analytical beds and up to ten guard beds are achievable within a separating device.

In these separating devices the stationary phase of the analytical media and guard media are selected from the group consisting of the set of ion exchange phase, reversed phase, size exclusion phase and affinity phase. The nanocolumn sized separating devices with guard beds are adapted to be cleavable at a boundary between the separating frit and the media disposed toward the receiving end of the first tube. Some of the separating devices have at least one marking on the outer surface of the first tube indicating the location of that boundary to facilitate such cleaving.

The process of making a separation device with two analytical beds in a first tube having a cylindrical wall having an inner surface defining a chamber with a first diameter, an exterior surface defining a second diameter, a first end for discharging a fluid and a second end for receiving a fluid starts by forming a first section in the chamber. This process involves securing a first end frit in an end of the first tube, loading and packing an analytical media behind the first end frit forming a packed analytical bed, placing a separating frit behind the packed analytical bed and loading and packing a second analytical media behind the separating frit forming a second packed analytical bed. The separating device may be further processed by securing a second end frit behind the second packed analytical bed. Other separation devices are made by repeating the operations of placing of the separating frit and loading and packing the analytical media up to nine additional times. In one method of making the separation device, the first end frit is a length of a second tube and the separation device, the separation frit is a length of a second tube. In another method of making the separation device, the first end frit is formed in situ as an immobilized stationary phase, where the stationary phase material is suspended in a polymeric network (a PDMS frit) in an end of the first tube. In one method of making the separation device, the separation frit is formed as a depth of glass microspheres.

In using the separating device with guard bands, A sequence of samples are run through the column and an analytical device to determine the components of each sample. The results will have peaks at known times indicating the components. As the column becomes clogged with debris, overall chromatographic performance deteriorates as is known in the industry. In particular, the peaks will broaden making it harder to interpret the results. When the guard band is cleaved from the column chromatographic performance is restored.

The features and advantages of this invention will be apparent from the following, more detailed description when considered in connection with the accompanying drawings, wherein like features are identified by like numerals.

DETAILED DESCRIPTION

Figure 1:
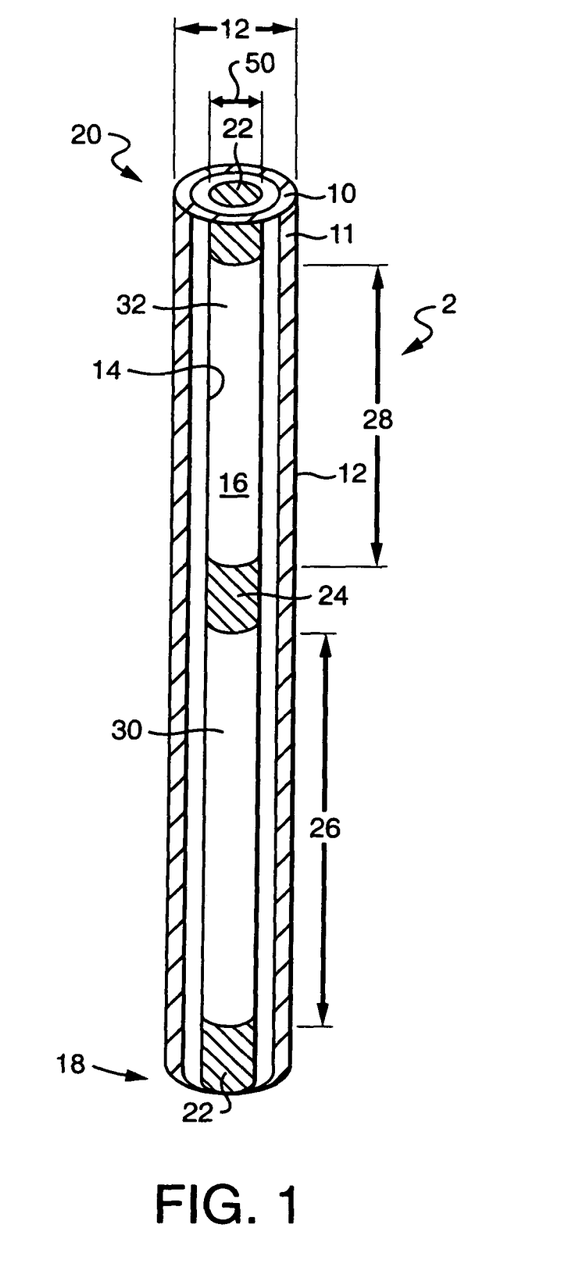
FIG. 1 is a representation of a guarded column according to the invention.

The present invention is directed to a separation device as shown in FIG. 1. The separation device 2 comprises a first tube 10 having a cylindrical wall 11 with an inner surface 14 defining a chamber 16 having a first diameter 13, an exterior surface 12 defining a second diameter 15, a first end 18 and a second end 20. The second end 20 receives a fluid containing the sample and the first end 18 discharges a separated fluid. In one embodiment, chamber 16 has a first section 26 and second section 28 as shown in FIG. 1. It is within the scope of the invention for the number of second sections to be less than or equal to ten. The first section 26 is adapted for containing a first media, which typically forms a first analytical bed 30. The second section 28 is adapted for containing a second media, which forms a second bed 32, where the second bed 32 is either a second analytical bed or a guard bed. When the first media is contained within the first section 26 and the second media is contained within the second section 28, a separating frit element 24 is disposed within the first tube between the first and second sections 26, 28 to separate the medias. At least one end frit element 22 is secured to the inner surface 14 of the first tube 10 to contain the medias in the first tube 10.

When the separating device 2 is formed as a guarded column as illustrated in FIG. 1, the analytical bed 30 is formed near the first end 18 of the device 2 with an end frit 22 to allow the analytical bed 30 to be formed and packed to a precise length. The separating frit 24 prevents the medias in the two sections 26, 28 from mixing and assures that the length of the analytical bed is as specified. The guard bed 32 formed behind the separating frit 24 in the second section 28 either extends to the end of the first tube 10 or is topped by a second end frit 22 to secure the material in the chamber 16.

Figure 2:
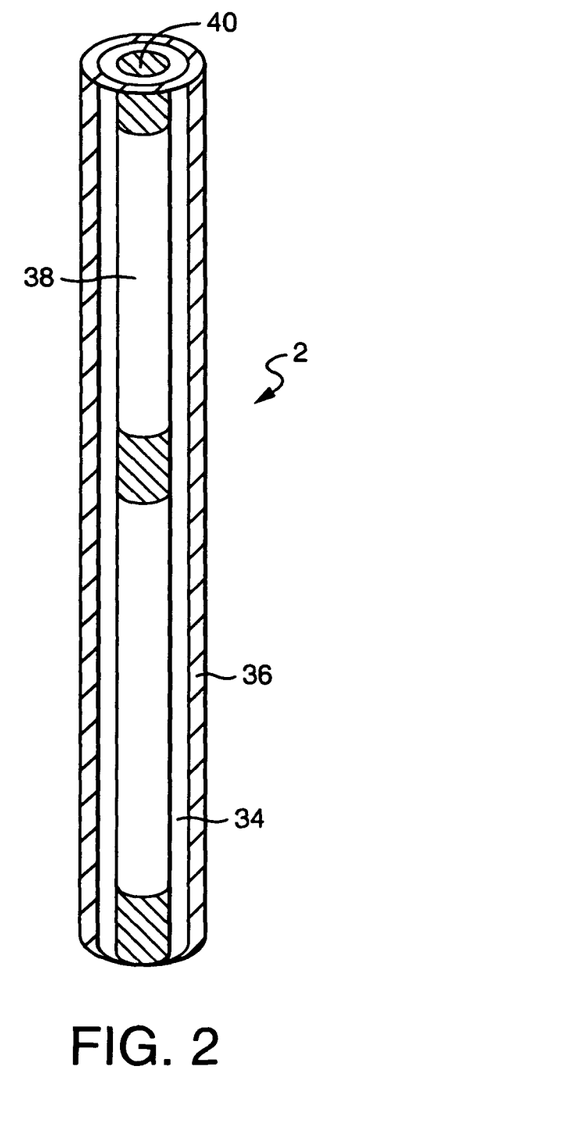
FIG. 2 is a representation of a multi-use column according to the invention.

When the separating device 2 is formed as a multi-use column as shown in FIG. 2, a second analytical bed 38 replaces the guard bed 32. This second analytical bed 38 is formed from the same or a different media depending on the intended application. For instance, if the application were peptide analysis, both the first and second media could be an activated carbon such as $C_{18}$ from Waters Co. of Milford Mass.; whereas if the application were a protein analysis, the first media would be chosen from a ion exchange media and the second media would be chosen from a reverse phase media. The lengths of the beds shown are for illustration purposes only. Those skilled in the art can determine the volume of stationary phase needed for an intended separation.

In one embodiment, illustrated in FIG. 2, the first tube 10 of the separation device 2 is made of a capillary tube. When the separation device 2 is being used for liquid chromatography, the capillary tube 34 is preferably formed of fused silica. Since the fused silica is fragile, the outside surface is typically coated with a layer of polyimide 36 for protection. The first diameter of the capillary tube used in the separation device 2 is between 25 μm and 180 μm, with a preferred range of between 70 μm and 110 μm. In embodiments at the capillary scale, it is desirable to have the end frit element 22 fit in the tube 10 with the end surface 40 of the frit aligned with its end of the first tube 10. This alignment limits dead space when the separation device 2 is connected to a transfer tube (not shown) so that bandspreading is minimized.

Figure 3:
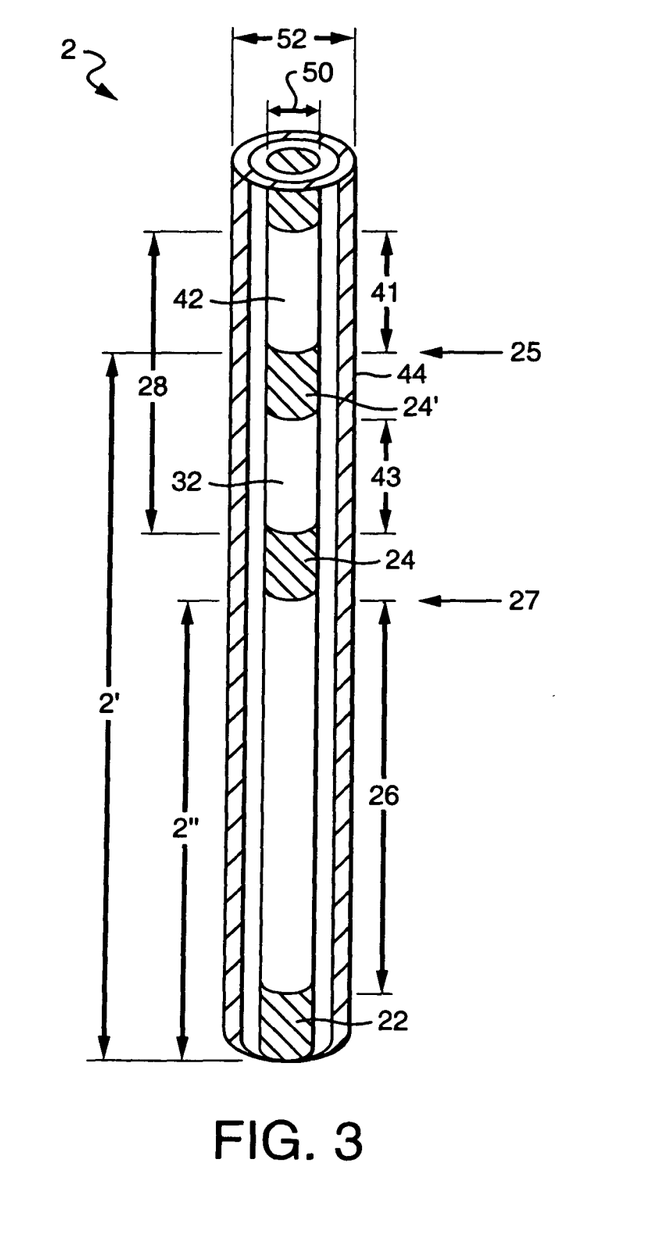
FIG. 3 is a representation of a multi-guard column according to the invention.

In another embodiment shown in FIG. 3, the separating device 2 further comprises an additional section 41 in the chamber 16, where the length of the former second section 28 may be regarded as divided into a new second section 43 and the additional section 41. The additional section 41 is adapted for containing a third media. This embodiment uses a second separating frit element 24' placed between the second media in the new second section 43 and the third media in the additional section 41. The additional section 41 allows for various configurations of the separating device 2 with the first media formed as a first analytical bed, the second media formed either as a second analytical bed or as a guard bed and the third media formed as a guard bed. Separation devices 2 with up to two analytical beds and up to ten guard beds (for a total of 11 beds) are practical.

The capillary sized separation devices with multiple guard beds, such as that illustrated in FIG. 3, are particularly well suited for use with samples incorporating large molecules that typically clog separation devices. When the separation device 2 becomes clogged, as indicated by the reduced resolution of the peaks, the outermost guard bed 41 is removed by cleaving the separation device 2 at the input end 25 of the separation frit 24'. The shortened separation device 2' is then available for further analyses until the second guard bed 43 becomes clogged. The second guard bed 43 is removed by cleaving the shortened separation device 2' at the input end 27 of the first separation frit 24. The further shortened separation device 2" is then available for further analyses until the analytical column becomes clogged. The separation device with clogged analytical column is disposed of after performing many more analyses than a separation device that did not incorporate any guard beds.

Figure 4:
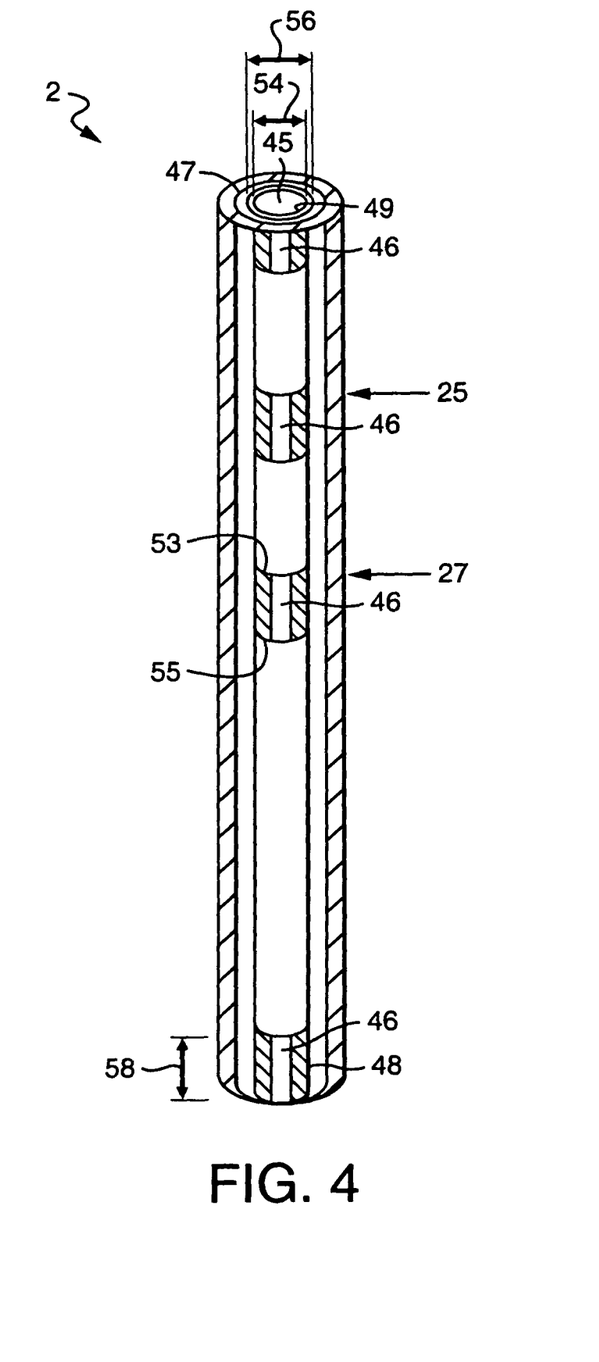
FIG. 4 is a representation of a multi-guard column made with capillary frits according to the invention.

In one embodiment of capillary separation devices, as shown in FIG. 4, at least one frit element is implemented as a second tube 46 having a second cylindrical wall 47 about a cavity 45 with a second inner surface 49 defining a third diameter 54, a second exterior surface 28 defining a fourth diameter 56, a third end 55 and a fourth end 53. When installed, the fourth diameter 56 cooperates with the first diameter 50 to contain at least one media. In particular, the fourth diameter 56 is only slightly smaller than the first diameter 50 so that the second tube 46 is oriented in the first tube 10 by friction. In one instance, the difference between the fourth diameter 56 and the first diameter 50 is approximately 10 μm. In one instance, the second tube 46 used as a separation frit has a length 58 of approximately 1 cm. The ends of the second tube 46 are oriented perpendicular to a length 58 of the second tube 46 providing a flat surface that aligns with the ends of the first tube 10. The third diameter 54 is significantly smaller than the first diameter 50 to limit any migration of the media through the cavity 45 formed in the second tube 46. In one instance, the third diameter 56 is approximately 20% of the first diameter 50. When second tube 46 forms an end frit 22, the second tube 46 is stabilized in place with an adhesive. In one embodiment, one of the end frit elements 22 formed of a second tube 46 has an end aligned with the respective end of the first tube 10 leaving no dead space, which is associated with bandspreading.

In one embodiment, a longer second tube 46 functioning as an end frit element 22 is disposed in the first end 18 for discharging fluid. When the length of the second tube 46 is approximately 6 cm or longer, with only approximately 1 cm fixed in the first end 18, this end frit element functions as a transfer tube (not shown) for transporting the fluid from the separating device 2. A separation device 2 of this type minimizes the bandspreading introduced when a separate transfer tube is attached. Further, the transfer tube can be directly connected to a detector associated with the separation device 2.

Figure 5:
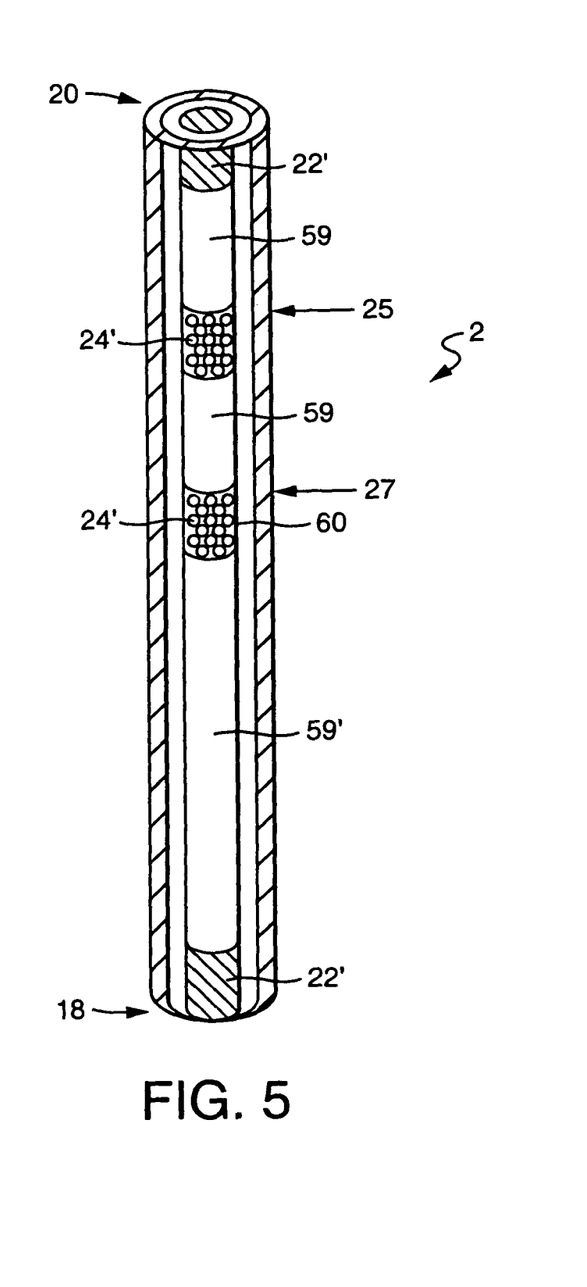
FIG. 5 is a representation of a multi-guard column made with PDMS and glass microsphere frits according to the invention.

In an alternate embodiment of the separating device as illustrated in FIG. 5, at least one end frit element 22' is formed as an intimate mixture of particles comprising a stationary phase material and a polymeric network comprising cross-linked poly(diorganosiloxane), wherein the particles are suspended in the polymeric network. In a particular implementation, the poly(diorganosiloxane) is poly(dimethysiloxane), and the resulting frit is termed a PDMS frit.

In one embodiment, the at least one separating frit 24' is composed of a layer of glass microspheres 60. The layer of glass microspheres 60 is between approximately 200 and 500 μm thick. A preferred thickness is approximately 250 μm. The glass microspheres 60 have a diameter of between approximately 3.5 and 5 μm. with a preferred diameter of approximately 5 μm. The separating frit 24' separates the media and allows the analytical and guard beds to be packed to a specified length. While glass beads are preferred and beads incorporating polymer are not appropriate, other non-adsorbing beads may be used.

FIG. 5 illustrates a separation device 2 formed with two PDMS end frits 22', three beds 59, and two separation frits 24' formed of glass microspheres 60. The separation device illustrated has the bed 59' closest to the discharge end 18 formed as an analytical bed and the other beds 59 formed as guard beds. The first cleavage point 25 is directly above the separation frit 24' toward the input end 20 and the second cleavage point 27 is directly above the second separation frit 24∝ from the input end 20.

In these various separating devices 2, the stationary phase of analytical media are selected from any of the stationary phases that are utilized in the industry. In particular, the stationary phase is selected from the group consisting of ion exchange phase, reversed phase, and solid phase extraction phase. The separating devices 2 with guard beds 32 are adapted to be cleavable at a boundary 27, 44 between the separating frit 24 and the media disposed toward the first end 18 of the first tube 10. Some of the separating devices 2 have at least one marking on the outer surface 12 of the first tube 10 indicating a location of the boundary 27 between the separating frit 24 and the media disposed toward the second end 20 of the first tube 10 to facilitate such cleaving.

Figure 6:
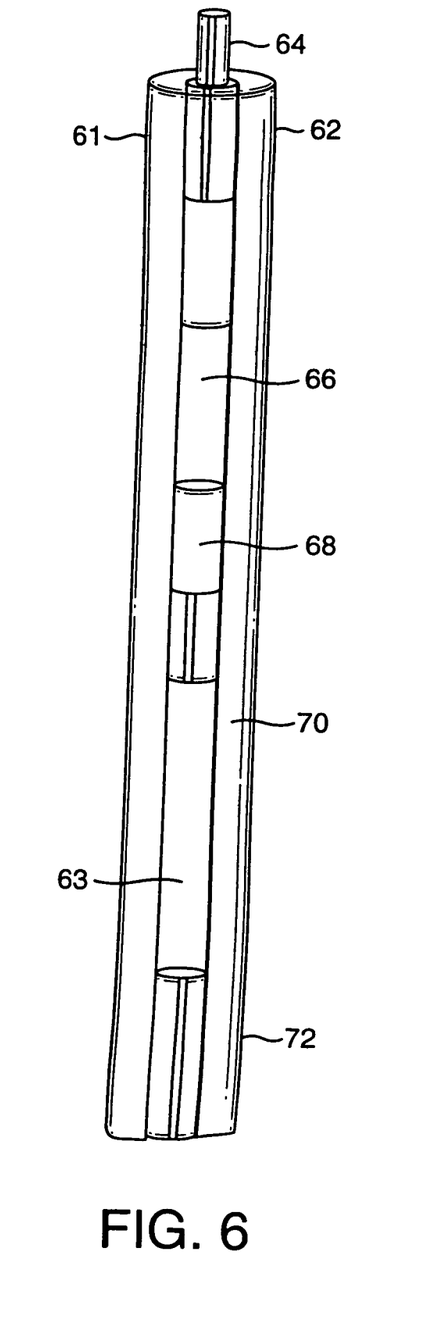
FIG. 6 is picture of a guarded column made according to the invention.

FIG. 6 is a picture of a capillary sized separation device made utilizing frits formed of second tubes. The first tube 10 forms the outer walls 61 and the chamber 63 within the outer walls 61 of the device. An inlet tube 64 is connected to a source (not shown) and is pressed against the inlet end frit 62. Guard region 66 is made up of stationary phase between the inlet end frit 62 and the separation frit 68. Analytical region 70 is made up of stationary phase between the separation frit 68 and the outlet end frit 72. For reference only, the dimensions of the illustrated separation device are approximately 14 cm long with a 10 cm analytical bed, a 2 cm guard region and outlet and frits of approximately 1 cm in length.

The method for making a separation device with two analytical beds and two guard beds is detailed below to illustrate the process. The device is made by selecting a first tube of the appropriate diameter and length, where the cylindrical wall encloses a chamber for receiving material with the inner surface of the cylindrical wall defining the device inner diameter. A set of stationary phases specific to the targeted application is assembled for packing into the device to form the sequence of beds. The first tube is held vertically with the downward end designated the outlet end. A first end frit is secured in the outlet end with the frit flush with the end of the first tube. The first stationary phase analytical media is loaded and packed into the chamber behind the end frit forming the first analytical bed. A separating frit is placed atop the first analytical bed to separate the bed from material subsequently loaded into the device. The second stationary phase for forming the second analytical bed is loaded and packed into the chamber behind the separating frit. A second separating frit is placed atop the second analytical bad to separate the bed from material subsequently loaded into the device. A third stationary phase for forming the first guard bed is loaded and packed into the chamber behind the second separating frit. A third separating frit is placed atop the first guard bed to separate the bed from material subsequently loaded into the device. A fourth stationary phase for forming the second guard bed is loaded and packed into the chamber behind the third separating frit. A second end frit is secured in the outlet end with the frit flush with the end of the first tube, or recessed a specified depth so that an inlet tube can be inserted to deliver a fluid.

While the method above creates a particular separation device, it is to be understood that devices with only one analytical bed, with up to ten guard beds, with the same stationary phase material used in various beds and without a second end frit are all encompassed in the teaching herein.

In one option for the method of making the separation device 2, the first end frit 22 is a length of a second tube 46, where the outer diameter 56 of the second tube 46 is only slightly smaller than the inner diameter 50 of the first tube 10. The second tube 46 is secured in the end 18 of the first tube 10 by an adhesive. In another option, the separation frit 24 is a length of second tube 46, where the outer diameter 56 of the second tube 46 is only slightly smaller than the inner diameter 50 of the first tube 10. The tube 46 of the separation frit 24 is not secured in the first tube but rather rests between two beds formed in the chamber. In another method of making the separation device 2, the first end frit 22 is formed in situ as a PDMS frit in an end 18 of the first tube 10. In another option of making the separation device 2, the separation frit 24 is formed as a layer of glass microspheres.

In using the separating device with guard bands, A sequence of samples are run through the column and an analytical device to determine the components of each sample. The chromatographic results have peaks at known times indicating the components. As the column becomes clogged with debris, overall chromatographic performance deteriorates as is known in the industry. In particular, the peaks will broaden making it harder to interpret the results. Those skilled in the art will recognize the deterioration. When the column peak width has increased by approximately 20% of the original value, the column has become essentially unusable. The guard band is then cleaved from the column and chromatographic performance is restored.

Those skilled in the art will recognize, or be able to ascertain using no more than routine experimentation, numerous equivalents to the specific procedures, embodiments, claims and examples described herein. Such equivalents were considered to be within the scope of this invention and covered by the claims appended hereto. The contents of all references, issued patents and published patent application cited throughout this application are hereby incorporated by reference. The invention is further illustrated by the following example.

Example I

I. Construction of Device—Utilizing Second Tube Frits

A nanocolumn utilizing second tube frits was prepared as follows. A 2 cm section of a 5 cm length of (20 μm×90 μm)(inner diameter×outer diameter) fused silica capillary, intended to act as a retaining frit, was inserted into a (100 μm×360 μm) fused silica capillary, which serves as the column housing. The smaller capillary was secured in place by coating 1.5 cm of the outer surface with poly(dimethylsiloxane) (PDMS) and re-inserting it into the 100 μm ID capillary. The entire assembly was placed in a 110° C. oven for 2 hours to cure the PDMS. After curing, the extra 3 cm of (20 μm×90 μm) capillary was cleaved using a ceramic scoring device. An analytical bed of 3.5 μm Symmetry® C18, (Waters Corp., Milford Mass.) or the like, was packed against the retaining frit to a length of 10 cm at 1000 psi, followed by a compression step at 4000 psi. After packing the analytical bed, a 1 cm section of (20 μm×90 μm) capillary was inserted and pushed to the top of the column bed with a 10 cm section of (20 μm×90 μm) capillary. Once the capillary separation frit was in place, a 2 cm bed of trapping/guard phase was packed at 2000 psi. A second 1 cm section of (20 μm×90 μm) capillary was placed at the head of this short bed as previously indicated. Upon fabrication of the desired number of trapping/guard beds, a final inlet frit was installed by using the aforementioned procedure for outlet retaining frit creation except that the PDMS was cured in the ambient overnight. The final column was not placed in the oven to cure the PDMS as this would cause rapid expansion of any residual solvents in the packed bed, resulting in destruction of the column.

II. Preliminary Evaluation of Device—Utilizing Second Tube Frits

A prototype nanocolumn device was constructed with the following bed sizes:
(1) Analytical bed: 100 mm 3.5 μm Symmetry® C18
(2) Guard#1: 1.5 cm 5.0 μm Symmetry® C18
(3) Guard#2: 1.5 cm 5.0 μm Symmetry® C18

Figure 7:
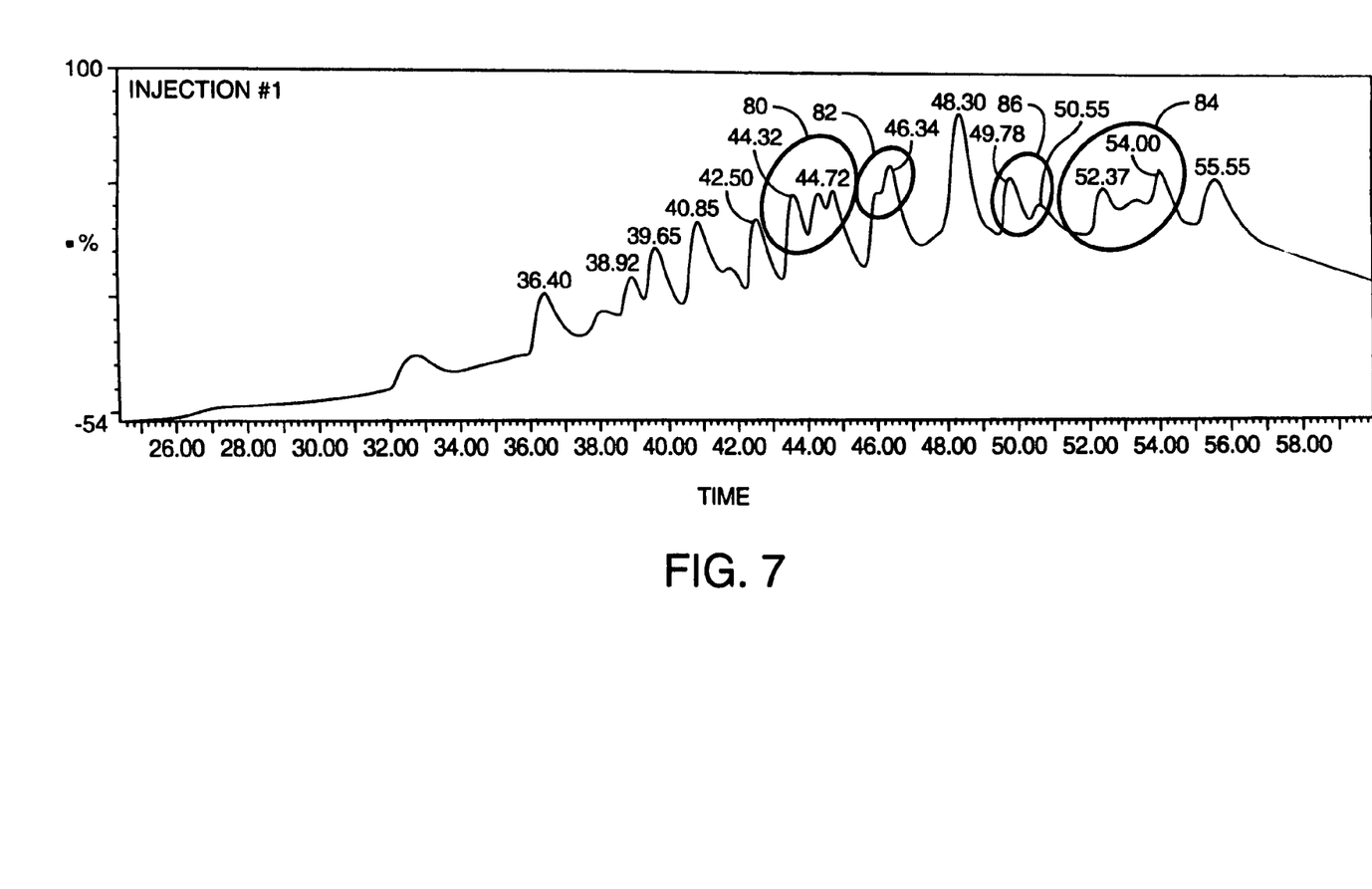
FIG. 7 is an output of a first run of an HPLC system using a guarded column according to the invention.
Figure 8:
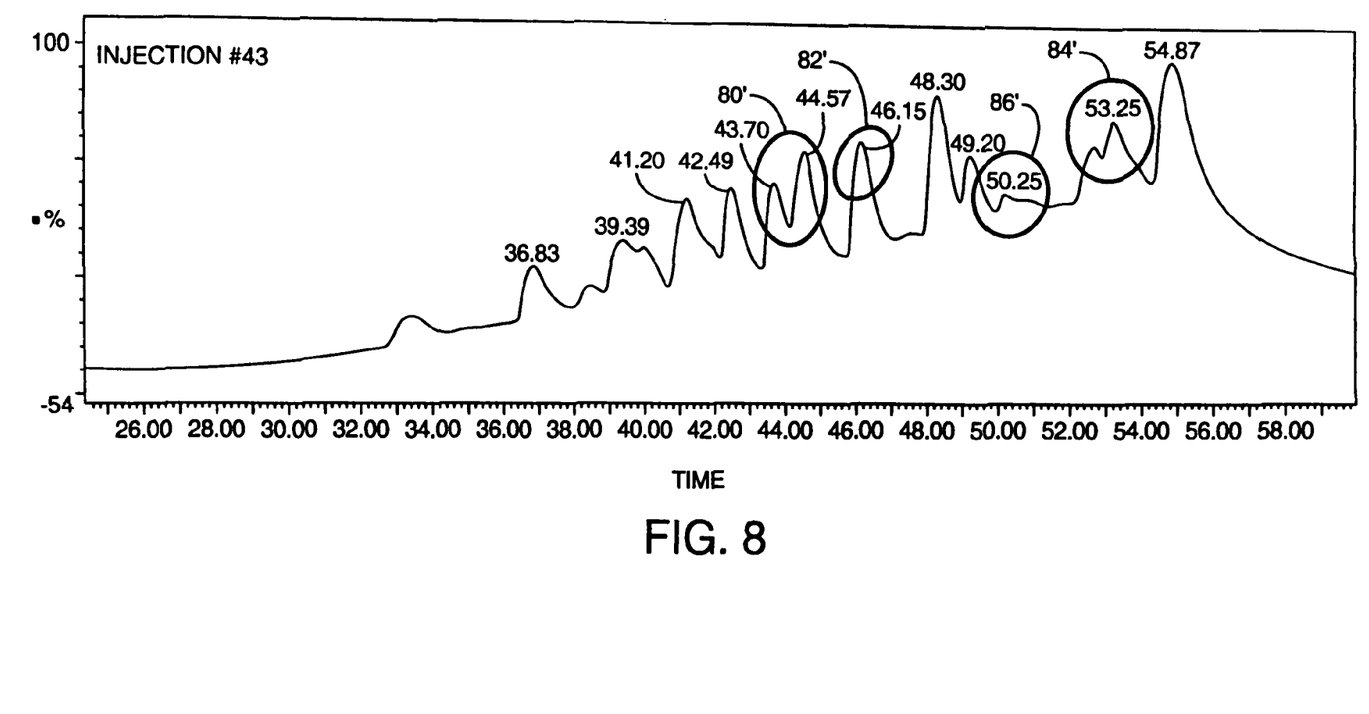
FIG. 8 is an output of the forty-third run of the HPLC system with the guarded column of FIG. 7.

In order to evaluate the performance of the prototype, an attempt was made to repeatedly overload the column. To this end, 50 replicate 1.0 μL injections of 5.0 μmol/μL enolase digest were made using a linear gradient comprised of 3-40% B (A: 0.1% TFA in water; B: 0.1% TFA in ACN) in 30 minutes at a flow rate of 400 nL/min. FIG. 7 is the chromatograph output of the prototype nanocolumn device after the first injection. Areas 80, 82, 84 and 86 are highlighted for comparison purposes. FIG. 8 is the chromatograph output of the prototype column after the forty-third injection. FIG. 8 illustrates the degradation in performance of the column as peptides begin to adsorb to the stationary phase, and the column begins to block. This was manifested by the loss of resolution between peaks 80 and 80', 82 and 82', 84 and 84' and 86 and 86'.

Figure 9A:
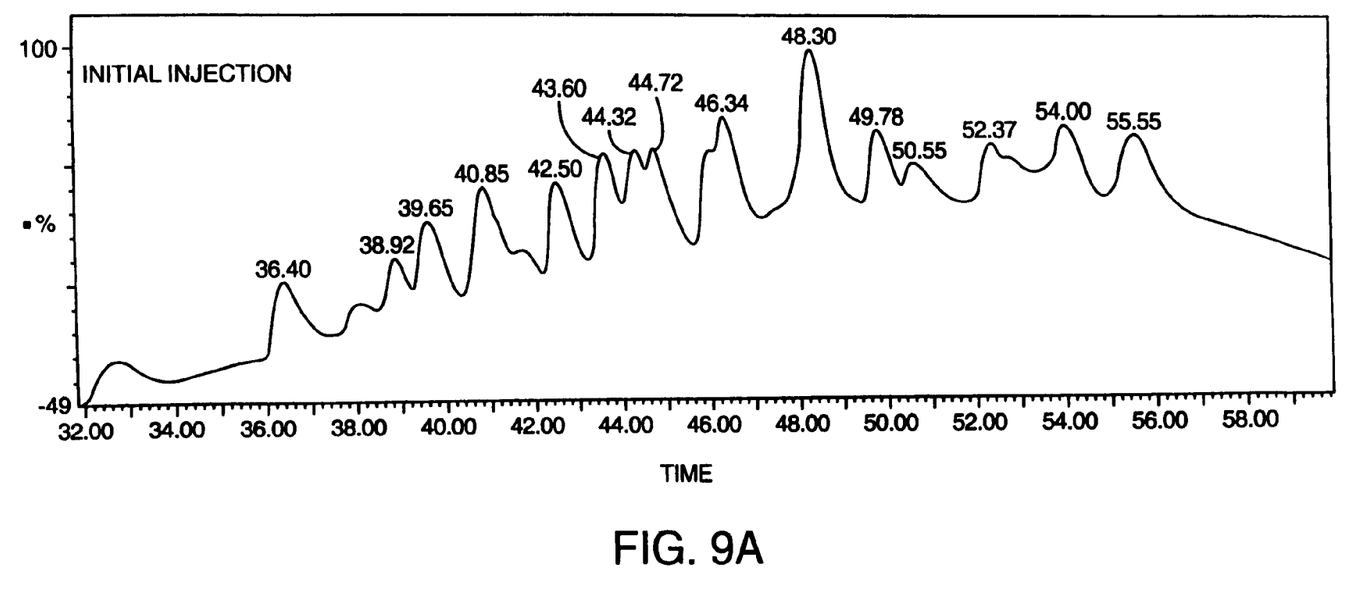
FIG. 9 is an output of the HPLC system after the first guard is removed from the guarded column of FIG. 7.
Figure 9B:
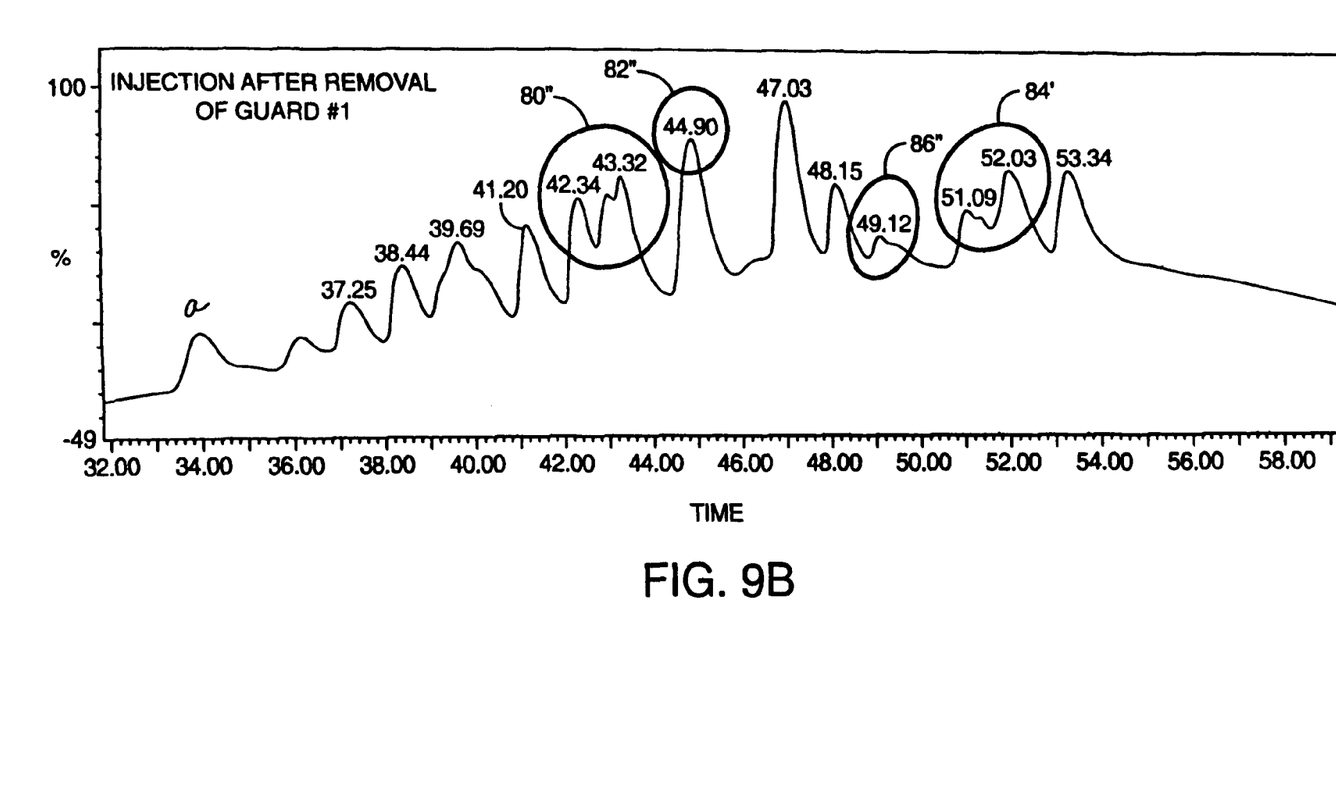

The first guard column was removed yielding the results shown in FIG. 9. Here, the column performance improves and some resolution was regained. There was a difference in retention time between FIGS. 7 and 9 due to the change in length of the column because the guard column has been cleaved off. However, comparing regions 80 and 80", 82 and 82", 84 and 84", and 86 and 86" illustrates how the resolution was restored by removing the clogged guard column.

One skilled in the art will appreciate further features and advantages of the invention based on the above-described embodiments. Accordingly, the invention is not to be limited by what has been particularly shown and described, except as indicated by the appended claims.

What is claimed is:

1. A separation column device comprising:
   a first tube having a cylindrical wall having an inner surface defining a chamber having a first diameter, an exterior surface defining a second diameter, a first end and a second end, said first end for discharging a fluid and said second end for receiving a fluid, said chamber having a first section and a second section;
   a first media contained within said first section, the first media being adapted to provide an analytical bed;
   a second media contained within said second section, the second media being adapted to provide a guard bed;
   a separating frit element disposed within said first tube between said first and second sections of said chamber, said separating frit element having a predesignated cleavage point at which said second section of the first tube is cleaved from the first tube after the guard bed provided by said second media has degraded from use of the separation column device, the predesignated cleavage point being located at a boundary between the separating frit element and the second section; and
   an end frit element secured to said inner surface of said first tube and securing at least one of said first media in said first section and said second media in the second section in the chamber of the first tube.

2. The separation column device of claim 1 wherein said end frit element has an end aligned with one of the ends of said first tube, in order to provide minimal dead space associated with bandspreading.

3. The separation device of claim 1 wherein said first diameter is between approximately 25 µm and 180 µm.

4. The separation column device of claim 1 wherein said first tube is formed of fused silica.

5. The separation column device of claim 1 wherein said first diameter is between 70 µm and 110 µm.

6. The separation column device of claim 1 wherein said end frit element is formed as an immobilized stationary phase comprising an intimate mixture of particles comprising a stationary phase material and a polymeric network.

7. The separating column device of claim 6 wherein said polymeric network is a cross-linked poly(diorganosiloxane) and wherein said particles are suspended in said poly(diorganosiloxane).

8. The separating column device of claim 6 wherein said poly(diorganosiloxane) is polydimethelseloxane (PDMS).

9. The separating column device of claim 1 further comprising a marking on said exterior surface of said first tube indicating a location of said cleavage point of said separating frit element.

10. The separating column device of claim 1 further comprising:
    an additional section in said chamber, said additional section for containing a third media; and
    an additional separating frit element, said additional separating frit element disposed between said second media in said second section and said third media in said additional section.

11. The separating column device of claim 10 wherein said third media is adapted to provide a second guard bed.

12. The separating column device of claim 11 wherein one of said second media adapted to provide a guard bed and said third media adapted to provide a second guard bed is composed of a stationary phase selected from the set of ion exchange phase, reversed phase, size exclusion phase and affinity phase.

13. The separating column device of claim 1 further comprising a plurality of additional sections in the chamber separated by fit elements, each additional section being adapted to provide a guard bed, and wherein a number of additional sections adapted to provide a guard bed is between one and nine.

14. The separating column device of claim 10 wherein at least one of said first media and said third media is composed of a stationary phase selected from the set of ion exchange phase, reversed phase, size exclusion phase and affinity phase.

15. The separating column device of claim 1 wherein said separating frit element is composed of a layer of glass microspheres.

16. The separating column device of claim 15 wherein a thickness of said layer of glass microspheres is between approximately 250 and 500 µm.

17. The separating column device of claim 15 wherein a thickness of said layer of glass microspheres is approximately 250 µm.

18. The separating column device of claim 15 wherein a diameter of said glass microspheres is between approximately 3.5 and 5.0 µm.

19. The separating device of claim 15 wherein a diameter of said glass microspheres is approximately 5.0 µm.

* * * * *

UNITED STATES PATENT AND TRADEMARK OFFICE
CERTIFICATE OF CORRECTION

| | | |
|---|---|---|
| PATENT NO. | : 8,685,239 B2 | |
| APPLICATION NO. | : 11/329759 | |
| DATED | : April 1, 2014 | |
| INVENTOR(S) | : Jennifer Harnisch Granger and Robert Plumb | |

It is certified that error appears in the above-identified patent and that said Letters Patent is hereby corrected as shown below:

In the Claims

Claim 13, Column 10, Line 26:
• Replace the word "fit" with the word "frit".

Signed and Sealed this
Twenty-second Day of July, 2014

Michelle K. Lee
*Deputy Director of the United States Patent and Trademark Office*